US007067269B2

(12) United States Patent
Drees et al.

(10) Patent No.: US 7,067,269 B2
(45) Date of Patent: Jun. 27, 2006

(54) ASSAYING APPARATUS, KIT, AND METHOD FOR LIPIDS AND ASSOCIATED ENZYMES

(75) Inventors: Beth E. Drees, Park City, UT (US); Glenn D. Prestwich, Salt Lake City, UT (US); Paul O. Neilsen, Draper, UT (US); Leena Chakravarty, Sandy, UT (US); Michael J. Mostert, Salt Lake City, UT (US)

(73) Assignee: Echelon Biosciences, Inc., Salt Lake City, UT (US)

( * ) Notice: Subject to any disclaimer, the term of this patent is extended or adjusted under 35 U.S.C. 154(b) by 94 days.

(21) Appl. No.: 09/991,933

(22) Filed: Nov. 26, 2001

(65) Prior Publication Data

US 2003/0100028 A1 May 29, 2003

(51) Int. Cl.
*G01N 33/53* (2006.01)

(52) U.S. Cl. .................. 435/7.93; 435/7.1; 436/164; 436/172

(58) Field of Classification Search .............. 435/7.1, 435/7.92, 7.93, 975; 436/518, 524, 164, 436/172
See application file for complete search history.

(56) References Cited

U.S. PATENT DOCUMENTS

| 5,420,016 | A | * | 5/1995 | Boguslaski et al. ........... 435/12 |
| 5,731,415 | A | | 3/1998 | Gazzano-Santoro et al. |
| 5,741,689 | A | | 4/1998 | Dhand et al. |
| 5,824,492 | A | | 10/1998 | Hiles et al. |
| 5,846,824 | A | | 12/1998 | Hiles et al. |
| 5,885,777 | A | | 3/1999 | Stoyanov et al. |
| 5,948,664 | A | | 9/1999 | Williams et al. |
| 5,955,277 | A | | 9/1999 | Hansen et al. |
| 5,972,595 | A | | 10/1999 | Kasila et al. |
| 6,001,354 | A | | 12/1999 | Pot et al. |
| 6,043,062 | A | | 3/2000 | Klippel et al. |
| 6,194,173 | B1 | * | 2/2001 | Czech et al. ............... 435/69.1 |
| 6,238,903 | B1 | | 5/2001 | Krystal |
| 6,274,327 | B1 | | 8/2001 | Hiles et al. |
| 6,291,220 | B1 | | 9/2001 | Williams et al. |
| 6,300,111 | B1 | | 10/2001 | Klippel et al. |
| 6,436,671 | B1 | | 8/2002 | Domin et al. |
| 6,482,623 | B1 | | 11/2002 | Vanhaesebroeck et al. |
| 6,531,283 | B1 | * | 3/2003 | Kingsmore et al. ............ 435/6 |
| 6,645,724 | B1 | * | 11/2003 | Ding et al. ................... 435/7.1 |
| 6,753,157 | B1 | * | 6/2004 | Goueli ........................ 435/7.4 |
| 2002/0028477 | A1 | | 3/2002 | Goueli et al. |
| 2002/0177166 | A1 | * | 11/2002 | Guthridge et al. ........... 435/7.1 |
| 2003/0235865 | A1 | * | 12/2003 | Epps et al. .................. 435/7.1 |
| 2004/0022677 | A1 | * | 2/2004 | Wohlstadter et al. ......... 422/52 |

FOREIGN PATENT DOCUMENTS

| WO | WO 97/46688 | 12/1997 |
| WO | WO 98/15629 | 4/1998 |
| WO | WO 01/92560 | 12/2001 |
| WO | WO 02/12276 | 2/2002 |
| WO | WO 03/046202 | 6/2003 |

OTHER PUBLICATIONS

Klarlund et al., Signaling by Phosphoinositide-3,4,5-trisphosphate Through proteins Containing Pleckstrin and Sec7 Homology Domains, Science, vol. 275, pp. 1927-1930, 1997.*
Klarlund. J. et al, Signaling by Phosphoinositide-3, 4,5-Trisphosphate Through Proteins Containing Pleckstrin and Sec7 Homology Domains, Science, vol. 275, 1927-30 (1997).
Roymans, D. et al, Phosphatidylinositol 3-kinases in tumor progression, *Eur J Biochem*, vol. 268, 487-98 (2001).
Franke, T. et al, PI3K: Downstream AKTlon Blocks Apoptosis, *Cell*, vol. 88, 435-7 (1997).
Klippel, A. et al, Activation of Phosphatidylinositol 3-Kinase is Sufficient for Cell Cycle Entry and Promotes Cellular Changes Characteristic of Oncogenic Transformation, *Mol Cell Biol*, vol. 18, No. 10, 5699-711 (1998).
Dowler, S. et al, Identification of pleckstrin-homology-domain-containing proteins with novel phosphoinositide-binding specificities, *Biochem J*, vol. 351, 19-31 (2000).
Frech, M. et al, High Affinity Binding of Inositol Phosphates and Phosphoninositides to the Pleckstrin Homology Domain of RAC/Protein Kinase B and Their Influence of Kinase Activity, *Journal of Biological Chemistry*, vol. 272, No. 13, 8474-81 (1997).
Phillips, W. et al, Increased Levels of Phosphatidylinositol 3-Kinase Activity in Colorectal Tumors, *Cancer*, vol. 83, No. 1, 41-47, (1998).
Bird, I., Analysis of Cellular Phosphoinositides and Phosphoinositols by Extraction and Simple Analytical Procedures, *Methods Mol Biol*, vol. 27, 227-248 (1994).
Chan, A. et al, CD7-mediated regulation of integrin adhesiveness on human T cells involves tyrosine phosphorylation-dependent activation of phosphatidylinositol 3-kinase, *Journal of Immunology*, 159(2), 934-942 (1997).

(Continued)

Primary Examiner—Long V. Le
Assistant Examiner—Gary W. Counts
(74) Attorney, Agent, or Firm—The McCallum Law Firm

(57) ABSTRACT

A lipid assay method, kit, and apparatus involving exposure of a protein, having a lipid recognition motif that interacts with a target lipid and a competing lipid, to a solution containing the competing lipid, and determining whether the target lipid is present in the solution. The target lipid has a stronger affinity to the lipid recognition motif than does the competing lipid. The lipid recognition motif is preferably a pleckstrin homology (PH) domain, with the target lipid being a phosphoinositide. The assay determines activity of a lipid kinase, the target lipid being a phosphorylation product of a reaction between the lipid kinase and a substrate lipid. The assay can be a cancer screening method for detection of cancer cells, where detection of certain levels of a PI(3,4,5)P$_3$ target lipid is an indicator of a cancer cell.

10 Claims, 7 Drawing Sheets

OTHER PUBLICATIONS

Gray, A. et al, The pleckstrin homology domains of protein kinase B and GRP1 (general a\receptor for phosphoinositides-1) are sensitive and selective probes for the cellular detection of phosphatidylinositol 3,4-bisphosphate and/or phosphatidylinositol 3,4,5-trisphosphate in vivo, *Biochemical Journal*, 344(3), 929-936 (1999).

Kavran, J. et al, Specificity and Promiscuity in Phosphoinositide Binding by Pleckstrin Homology Domains, *Journal of Biological Chemistry*, 273(46), 30497-30508 (1998).

Piccione, E. et al, Phosphatidylinositol 3-Kinase p85 SH2 Domain Specificity Defined by Direct Phosphopeptide/SH2 Domain Binding, *Biochemistry*, vol. 32, No. 13, 3197-3202 (1993).

* cited by examiner

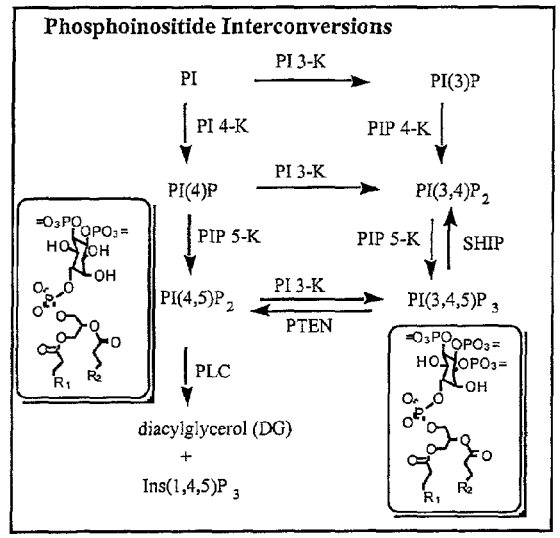
Fig. 1
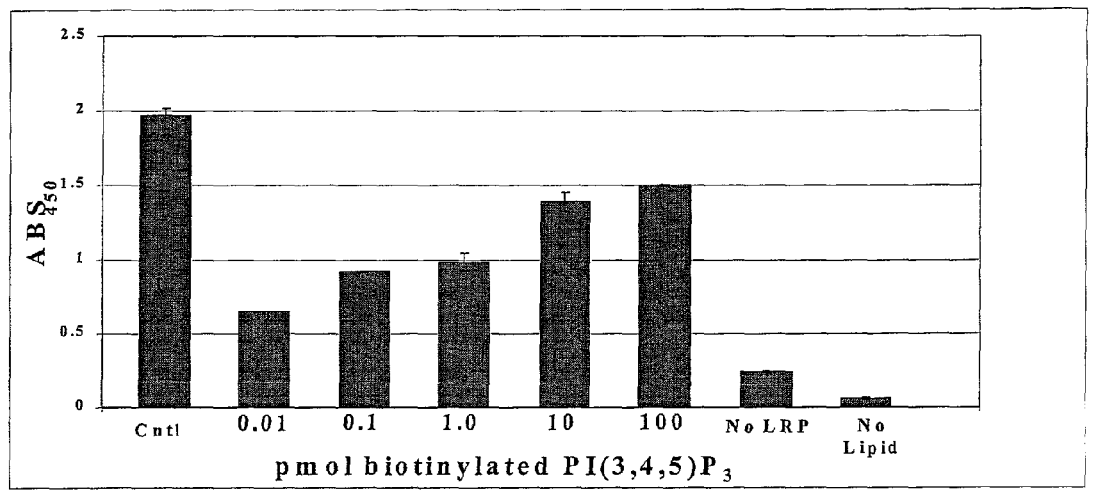
Fig. 2: ELISA PI(3,4,5)P₃ Binding assay

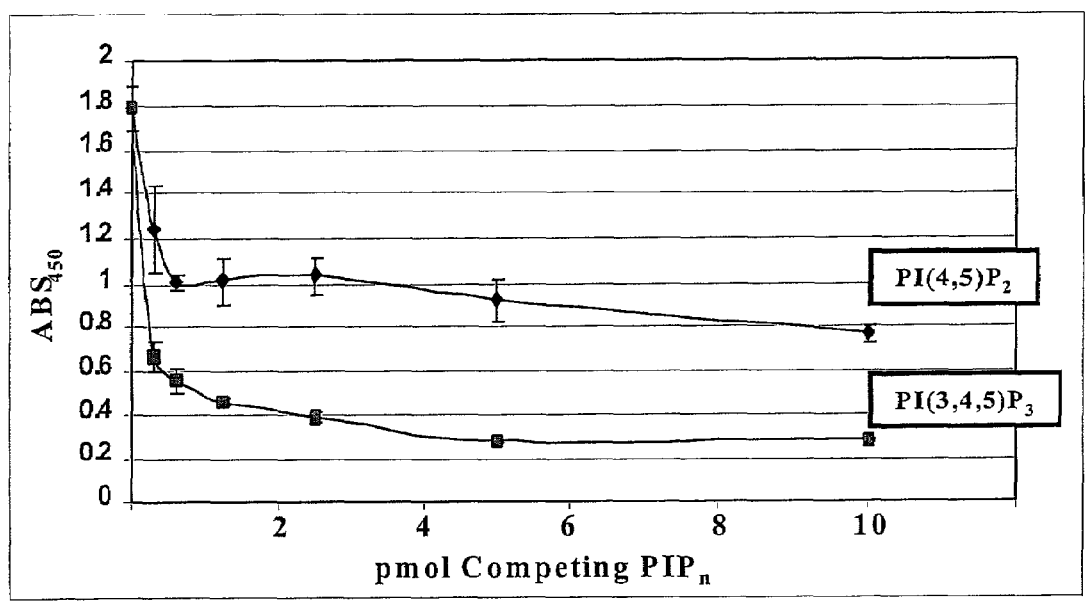
Fig. 3: PI(3,4,5)P$_3$ and PI(4,5)P$_2$ Competition Assay

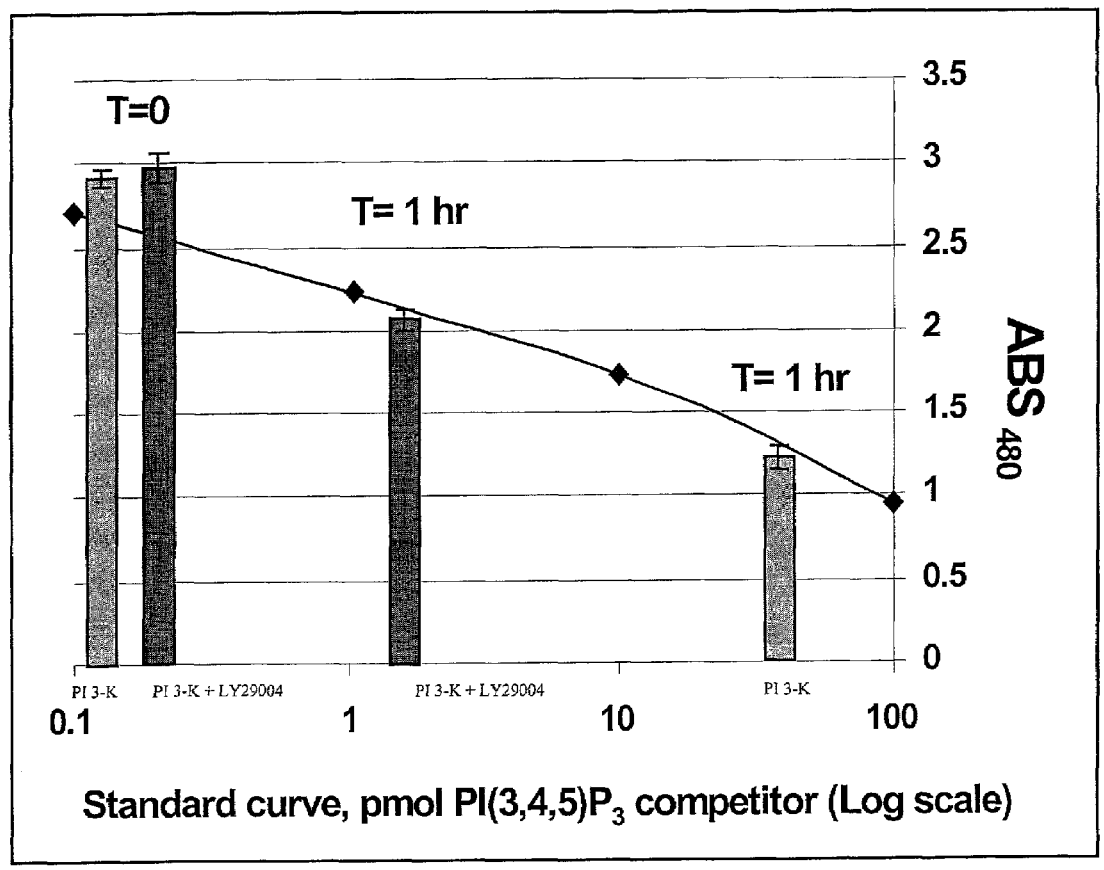
Fig. 4: Determination of PI 3-K α activity, ELISA Assay

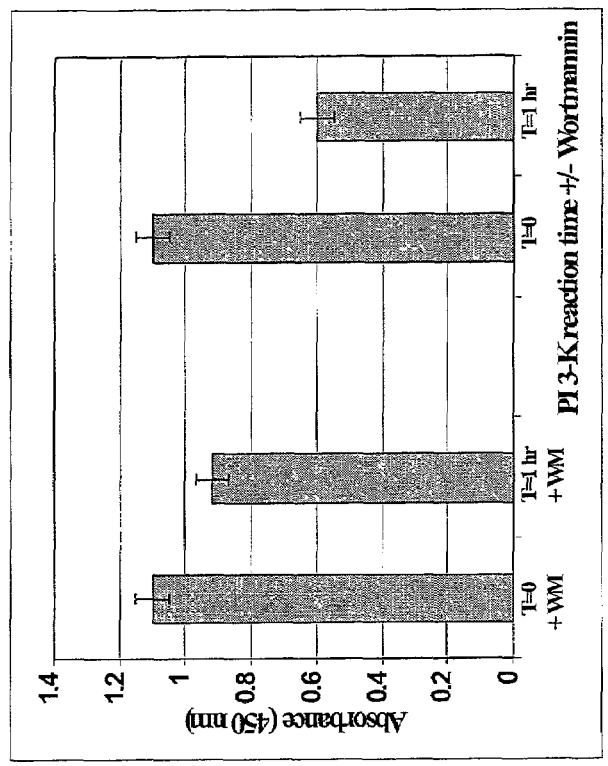
Fig. 6: Detection of PI 3-Kinase Activity in ELISA Assay
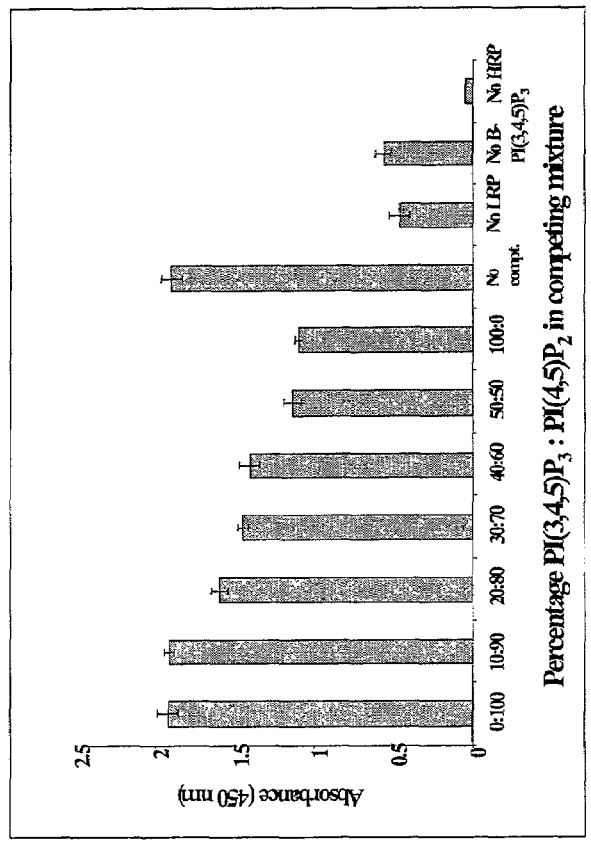
Fig. 5: Competition Between PI(3,4,5)$P_3$ & PI(4,5)$P_2$ for LRP Binding

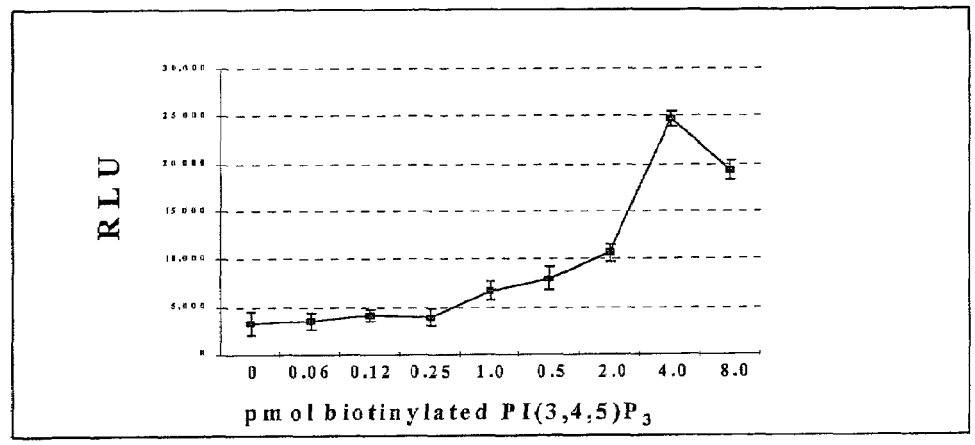
Fig. 7: PI(3,4,5)P$_3$ ALPHA Binding Assay
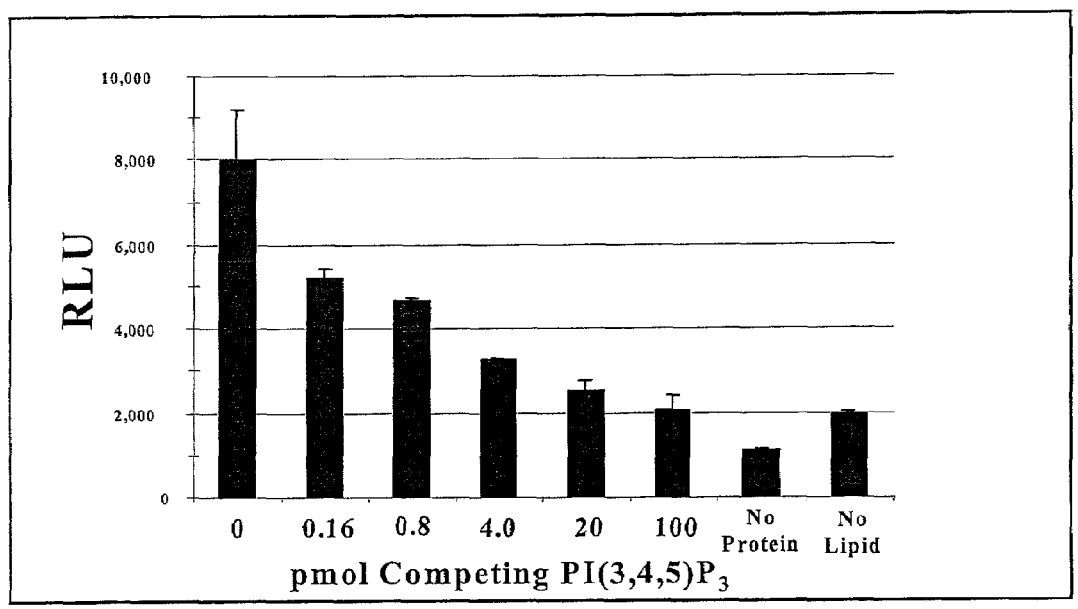
Fig. 8: PI(3,4,5)P$_3$ ALPHA Competition Assay

US 7,067,269 B2

ASSAYING APPARATUS, KIT, AND METHOD FOR LIPIDS AND ASSOCIATED ENZYMES

FIELD OF THE INVENTION

The present invention relates to enzymes that phosphorylate an inositol lipid, including phosphatidylinositol (4,5) bisphosphate (PI(4,5)P$_2$) and phosphoinositol (PdtIns) in general, at the D-3 position of the inositol ring. More particularly, the present invention relates to detection methods, kits, and apparatuses for detection of such enzymes.

BACKGROUND OF THE INVENTION

Phosphoinositides are key lipid second messengers in cellular signaling, with phosphatidylinositol (PI) dependent signaling pathways playing central roles in the regulation of many cellular processes. Disruption of these pathways is common to many disease states, including inflammation, diabetes, cardiovascular disease, and cancer. Because the activity of PI second messengers is determined by their phosphorylation state, the enzymes that act to modify these lipids are central to the correct execution of PI dependent signaling pathways.

In particular, phosphatidylinositol 3-kinase (PI 3-K) is important in pathways mediating cell proliferation, survival, differentiation and motility. Inhibitors of PI 3-K have been used to confirm the cellular functions of PI 3-K, but thus far, such inhibitors have not been deemed suitable for therapeutic uses because of problems such as toxicity and low selectivity. The PI 3-K family of heterodimeric lipid kinases is known primarily for its involvement in the phosphorylation of inositol lipids via transfer of the γ phosphate of ATP to the D-3 position of the inositol ring of PI, PI(4)P, and PI(4,5)P$_2$ giving rise to PI(3)P, PI(3,4)P$_2$, and PI(3,4,5)P$_3$ respectively. FIG. 1 shows an overview of these phosphoinositide metabolic pathways. PI(4,5)P$_2$ is a minor component of the plasma membrane's inner leaflet, and is part of a second messenger system that transduces many hormone signals. When not effected by PI 3-K, the PI(4,5)P$_2$ pathway includes a receptor with seven transmembrane segments, a heterotrimeric G-protein, and a specific protein kinase phopholipase C (PLC). Ligand binding to the receptor activates the G protein, G$_q$, whose membrane-anchored α subunit in complex with GTP diffuses laterally along the plasma membrane to activate the membrane-bound PLC. As shown in FIG. 1, the activated PLC catalyzes the hydrolysis of PI(4, 5)P$_2$ at its glycero-phospho bond, yielding inositol-1,4,5-trisphosphate (Ins(1,4,5)P3 and diacylglycerol (DG).

PI 3-kinase can be activated by tyrosine kinase receptors in response to growth factor stimulation. As discussed above, PI 3-kinase is then involved in catalyzing the formation of PI(3,4,5)P$_3$ via phosphorylation of its substrate (PI(4,5)P$_2$. By increasing cellular levels of PI(3,4,5)P$_3$, PI 3-K induces the formation of defined molecular complexes that act in signal transduction pathways. Notably, PI 3-K activity suppresses apoptosis and promotes cell survival through activation of its downstream target, PKB/Akt. PI(3, 4,5)P$_3$ signaling is regulated by its formation and by its conversion into PI(4,5)P$_2$. The lipid phosphatases PTEN and SHIP are two enzymes that both act to decrease the cellular levels of PI(3,4,5)P$_3$ by conversion either to PI(4,5)P$_2$ or PI(3,4)P$_2$.

There is considerable evidence that the activity of PI 3-K and the regulation of the level of its lipid products, in particular PI(3,4,5)P$_3$, is often defective in tumorigenesis, as reported in D. Roymans et al., *Phosphatidylinositol 3-kinases in Tumor Progression*, 268 Eur. J. Biochem. 487 (2001). PI 3-K activity and elevated PI(3,4,5)P$_3$ levels appear to contribute to cancer progression via constitutive activation of PKB/Akt, as reported in T. Franke et al., *PI3K: Downstream AKTion Blocks Apoptosis,* 88 Cell 437 (1997). Activated PKB/Akt provides a cell survival signal that blocks apoptosis and promotes survival following growth factor withdrawal or detachment from the cellular matrix. W. Phillips et al., *Increased Levels of Phosphatidylinositol 3-kinase Activity in Colorectal Tumors,* 83 Cancer 41 (1998) establish findings that elevated PI 3-K levels have been observed in some cancers. Further, experiments have indicated that cellular transformation is PI 3-K dependent. D. Roymans et al., 268 Eur. J. Biochem. 487, A. Klippel et al., *Activation of Phosphatidy linositol 3-kinase is Sufficient for Cell Cycle Entry and Promotes Cellular Changes Characteristic of Oncogenic Transformation,* 18 Mol. Cell Biol. 5699 (1998). The gene encoding the catalytic subunit of PI 3-K, PIK3CA, is an oncogene which is amplified in ovarian and cervical cancers. In addition, mutations that affect the regulation of PI 3-K signaling also contribute to tumorigenesis. PTEN is a tumor suppressor that is deleted or mutated in many cancer types. By converting PI(3,4,5)P$_3$ to PI(4,5) P$_2$, PTEN acts as a negative regulator of PKB/Akt activation by PI 3-K. Loss of PTEN activity results in abnormal activation of PKB/Akt and suppression of apoptosis. The lipid phosphatase SHIP also acts as a negative regulator PKB/Akt activity. Ablation of SHIP in transgenic mice leads to chronic hyperplasia, and loss of SHIP activity is one characteristic of chronic myelogenous leukemia, providing additional evidence linking the loss of regulation of PI(3,4, 5)P$_3$ levels with an abnormal proliferative state.

From the above discussion, it is clear that there is a need in the art for assaying methods and assay kits for measurement of either PI 3-K activity or presence of phosphoinositide products of PI 3-K activity in tissues, as such have the potential to become powerful molecular diagnostic tools. In addition, it is clear that there is a need in the art for assay platforms that are developed for measurement of PI3-K activity in clinical samples, and for use in vitro assaying methods for novel PI 3-K inhibitors.

SUMMARY OF THE INVENTION

It is an object of the present invention to meet the above-described needs and others. Specifically, it is an object of the present invention to provide a lipid assay method. The method includes the step of first exposing a protein, having a lipid recognition motif that interacts with a target lipid and a competing lipid, to a solution containing the competing lipid. The method further includes the step of determining whether the target lipid is present in the solution. According to the method, the target lipid has a stronger affinity to the lipid recognition motif than does the competing lipid.

According to one embodiment of the invention, the protein is Grp1, and the lipid recognition motif is a pleckstrin homology (PH) domain. Consequently, the target lipid is a phosphoinositide in this embodiment. In such a case, the Grp1 protein preferably contains a glutathionine-S-transferase fusion with the PH domain.

The assay determines activity of a lipid kinase, the target lipid being a phosphorylation product of a reaction between the lipid kinase and a substrate lipid. According to one embodiment of the invention, the lipid kinase is PI 3-kinase, and the target lipid is PI(3,4,5)P$_3$. In a most preferred embodiment of the invention, the lipid assay is a cancer screening method for detection of cancer cells, and detection of certain levels of the PI(3,4,5)P$_3$ target lipid is an indicator of a cancer cell.

The assay can be any of a number of assay types, but is preferably a plate-based assay. Examples include an enzyme linked immunosorbent assay (ELISA), an amplified luminescence proximity homogenous assay (ALPHA), and a fluorogenic assay.

In the embodiment where the assay is an ELISA assay, prior to exposing the protein having a lipid recognition motif to a target lipid and a competing lipid, a substrate of the assay plate can be coated with the competing lipid. Preferably, the coating step includes coating a streptavidin-coated substrate with the competing lipid.

Additional competing and noncompeting lipids can also be present in the solution, enabling the assay method of the present invention to be used with complex solutions including bodily tissues, fluids, and plasma.

The present invention is further directed to a lipid assay kit, which includes a target lipid, a competing lipid, and a protein that has a lipid recognition motif that interacts with the target lipid and the competing lipid. The target lipid has a stronger affinity to the lipid recognition motif than the competing lipid.

The assay kit can further include a multi-well assay plate. The multi-well assay plate preferably includes the competing lipid immobilized in wells of the multi-well assay plate.

The lipid assay kit can further include primary and secondary antibodies. As mentioned with respect to the assay method, additional competing and noncompeting lipids can also be present in the solution, enabling the assay method of the present invention to be used with complex solutions including bodily tissues, fluids, and plasma.

According to one embodiment of the invention, the protein is Grp1, and the lipid recognition motif is a pleckstrin homology (PH) domain. Clearly, however, the invention is easily adaptable to the use of other lipid receptor proteins or monoclonal antibodies. For example, various antibodies and lipid receptor proteins that are specific for PI(3,4,5)P3 or PI(3)P can be used in accordance with the invention. The protein preferably contains an affinity tag fusion with the lipid recognition motif. Examples of affinity tags include glutathionine-S-transferase, myc, or FLAG, etc. fused with a lipid recognition motif such as the 1 PH domain.

The target lipid is preferably a phosphoinositide. The assay kit is most preferably used for determination of activity of a lipid kinase. Thus, the target lipid would be a phosphorylation product of a reaction between the lipid kinase and a substrate lipid. The lipid kinase is preferably a PI 3-kinase, and the target lipid is preferably PI(3,4,5)P$_3$. The lipid assay is most preferably a cancer screening method for detection of cancer cells, and detection of a predetermined level of the PI(3,4,5)P$_3$ target lipid is an indicator of a cancer cell.

The assay can be any of a number of assay types, but is preferably a plate-based assay. Examples include an enzyme linked immunosorbent assay (ELISA), an amplified luminescence proximity homogenous assay (ALPHA), and a fluorogenic assay.

In the embodiment where the assay is an ELISA assay, prior to exposing the protein having a lipid recognition motif to a target lipid and a competing lipid, a substrate of the assay plate can be coated with the competing lipid. Preferably, the coating step includes coating a streptavidin-coated substrate with the competing lipid. Most preferably, the protein, target protein, and competing protein are not radiolabeled reagents.

The present invention is also directed to a multi-well plate for a lipid assay, which includes a lipid that is immobilized in wells of the multi-well assay plate. Another aspect of the invention is a method of making such a multi-well plate. The lipid can be immobilized in wells of the multi-well assay plate via, for example, a streptavidin-coating on a substrate of the wells. The multi-well plate is preferably used in an assay for determining activity of a lipid kinase. Most preferably, the lipid is a non-radiolabeled derivative of PI(3,4,5)P$_3$ such as, for example, biotinylated-PI(3,4,5)P$_3$.

Additional objects, advantages and novel features of the invention will be set forth in the description which follows or may be learned by those skilled in the art through reading these materials or practicing the invention. The objects and advantages of the invention may be achieved through the means recited in the attached claims.

To achieve these stated and other objects, the present invention may be embodied and described as set forth in the claims.

BRIEF DESCRIPTION OF THE DRAWINGS

The accompanying drawings illustrate the present invention and are a part of the specification. Together with the following description, the drawings demonstrate and explain the principles of the present invention.

FIG. 1 shows a diagram of phosphoinositide interconversions, including the phosphorylation of PI(4,5)P$_2$ to PI(3,4,5)P$_3$ using PI 3-K.

FIG. 2 shows a graphical representation of results of absorbance measurements representing the binding of the LRP detector protein to increasing amounts of immobilized PI(3,4,5)P$_3$ in an ELISA assay.

FIG. 3 shows a graphical representation of the results of a PI(4,5)P$_2$:PI(3,4,5)P$_3$ competition ELISA assay.

FIG. 4 shows a graphical representation of an ELISA quantitation of substrate conversion to PI(3,4,5)P$_3$ and the effect of the addition of inhibitor.

FIG. 5 shows a graphical representation of the results of a competition ELISA assay between PI(4,5)P$_2$ and PI(3,4,5)P$_3$ for LRP binding.

FIG. 6 shows a graphical representation of the results of in vitro detection of PI 3-kinase activity in an ELISA assay.

FIG. 7 shows a graphical representation of a PI(3,4,5)P$_3$ ALPHA binding assay.

FIG. 8 shows a graphical representation of a PI(3,4,5)P$_3$ ALPHA competition assay.

DETAILED DESCRIPTION OF THE PREFERRED EMBODIMENTS

Figure 9:
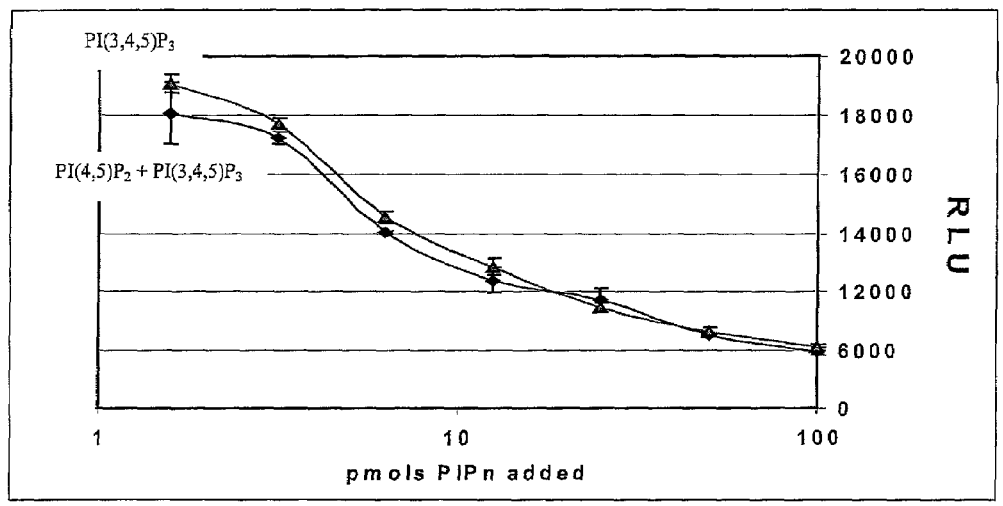
FIG. 9 shows a graphical representation of the ALPHA competition profiles of increasing PI(3,4,5)P$_3$ in a background of PI(4,5)P$_2$, and of a standard curve of increasing PI(3,4,5)P$_3$ competitor alone.

Using the drawings, the preferred embodiments of the present invention will now be explained. The present invention is directed to the use of lipid recognition proteins (LRP's) as detectors of target PIP$_n$s, in a convenient assay platform system that can be readily used in the industry.

LRP's that are used in accordance with the present invention can be recombinant proteins expressed as fusions of lipid recognition domains that are present in cellular proteins. The domains of the cellular proteins that interact with a lipid are fused to an affinity tag, such as glutathione-S-transferase (GST), myc, or FLAG, for example. The proteins having such domains are typically involved with such cellular functions as phosphorylation of lipids, or are adaptor proteins that assist in forming complexes with the cellular membrane to allow the cell membrane to interact with lipid structures. The domains from these proteins that allow the proteins to perform such functions can be extracted from the naturally occurring proteins, or prepared through recombinant methods, and then fused to GST to form an LRP.

For example, a group of proteins possess a certain type of pleckstrin homology (PH) domain which interacts specifically with the second messenger $PI(3,4,5)P_3$. Examples of these proteins include serine/threonine-specific protein kinases, PKB and PDK1, Bruton's tyrosine kinase BTK, the adaptor proteins DAPP1 and Bab1, as well as the ADP Ribosylation Factor (ARF), GTPase activating protein (GAP) centaurin-α, and the ARF guanine nucleotide exchange factor Grp1.

The PH domain is well known to those skilled in the art. Furthermore, different PH domains often exhibit specificity for different phosphoinosides. See Dowler et al., 2000 Biochem J. 351:19–31, which is incorporated herein by reference. Such domains are typically of ~100 residues, and are found in over 70 other known proteins. All PH domains are predicted to fold into a similar 3-dimensional structure, and may mediate protein-lipid interactions, protein-protein interactions, or both. Polypeptides with PH domains of determined tertiary structure include plecktrin, spectrin, dynamin, and phospholipase C-γ. The percentage of amino acid identity is poor between PH domains in general. However, there are certain positions that show high levels of residue type conservation. The residues thought to be required for high affinity interaction with $PI(3,4,5)P_3$ lie in the $PI(3,4,5)P_3$ Binding Motif (PPBM) near the N-terminal end of the PH domain. A single position near the C-terminal end of the PH domain shows complete identity throughout the domain family. Secondary structure predictions indicate that residues 450–530 of PDK1, for example, (positions 1–80) are likely to contain regions of β-sheet, while the residues between 531–550 (positions 80–100) are likely to form an extended α-helix, a prediction that is consistent with the known structures of other PH domains.

The molecular basis by which certain PH domains are able to interact with $PI(3,4,5)P_3$ has not been established definitively. However, reports have indicated that six conserved residues that lie at the N-terminal region of the PH domain in a K-X-Sm-$X_{6-11}$-R/K-X-R-Hyd-Hyd motif (where X is any amino acid, Sm is a small amino acid and Hyd is a hydrophobic amino acid), appear to correlate with high affinity binding of $PI(3,4,5)P_3$. In fact, most if not all specific $PI(3,4,5)P_3$ binding proteins identified possess this PPBM. The term PPBM is also known to those skilled in the art. The term "small amino acid" includes glycine, alanine, threoninie, and serine. An aspartate or proline amino acid residue may alternatively be present at the position in the motif where a small amino acid is preferred. The term "hydrophobic amino acid" includes tyrosine, leucine, isoleucine, tryptophan and phenylalanine. A glutamine amino acid residue may alternatively be present at the first position where a hydrophobic amino acid residue is preferred. A glutamine, asparagine or histidine amino acid residue may be present at a position where a lysine or arginine residue is preferred. It is strongly preferred that an acidic or hydrophobic residue is not present at a position where a lysine or arginine residue is preferred, or at the position in the motif where a small amino acid is preferred. It is preferred that the PH domain has at least five of the six specified residues of the PPBM. It is somewhat preferred that the PH domain has both hydrophobic amino acids of the motif and/or the first lysine (K) residue of the motif. It is preferred that the PH domain also has a tryptophan residue at the position equivalent to position 280 of TAPP1.

In a broad sense, the present invention involves methods, assay kits and apparatuses that use a specific LRP as a detection reagent for specific lipids in an enzyme assay for lipid metabolism. More particularly, the present invention involves the use of Grp1 as a cellular protein as a probe that interacts specifically with specific lipids in such assays. For example, the Grp1 protein includes a PH domain. While PH domains vary in the specificity of their interactions with various $PIP_n$s, the Grp1 PH domain exhibits a strong preference for interaction with $PI(3,4,5)P_3$. Thus, in a narrow sense, the present invention involves methods, assay kits and apparatuses that use a recombinant LRP containing a GST fusion with the Grp1 PH domain as a lipid detection probe.

Enzyme Linked Immunosorbent Assay (ELISA)

In order to readily distinguish $PI(3,4,5)P_3$ from other PIPs, a derivative such as biotinylated $diC_6$ $PI(3,4,5)P_3$ is immobilized in the wells of streptavidin-coated assay plates.

As an example, a 96-well plate can be used, although the present embodiment of the invention is clearly adaptable for a variety of assay plate sizes and formats. Initial experiments establish a range of LRP detector protein and biotinylated $PI(3,4,5)P_3$ where detection of the target phosphoinositide is optimized in an assay tray format. For example, in a standard curve binding procedure, a 96-well streptavin-coated assay plate marketed as StreptaWell® (Roche) is coated with increasing amounts of biotinylated $PI(3,4,5)P_3$ per well. The coated wells are then blocked for an hour at room temperature using 100 μl of Stabilguard® (SurMedics) per well. The samples are then incubated with 10 pmol of LRP in a 100 μl volume per well. Several washes are then performed. Next, 100 μl of a 1:1000 dilution of an anti-GST HRP-conjugated antibody, provided by Sigma, is added to each well. The GST HRP-conjugated antibody is provided as a reagent that interacts with the GST portion of the lipid recognition protein, and hence allows for subsequent colorimetric detection. After one hour of incubation at room temperature, the plates are washed and 100 μl of 3',3',5',5'-tetramethylbenzidine (TMB) substrate solution as a development reagent, obtainable from Sigma, is added to each well.

Following color development, the reaction is stopped by the addition of 100 μl 0.5 M $H_2SO_4$. Absorbance at 450 nm is measured. The results of the absorbance measurements representing the binding of the LRP detector protein to increasing amounts of immobilized $PI(3,4,5)P_3$ are shown in FIG. 2. As shown, the absorbance (450 nm) of samples having 10-fold incremental pmol amounts of biotinylated $PI(3,4,5)P_3$ are compared with a control, a sample containing no LRP detector protein, and a sample containing no biotinylated $PI(3,4,5)P_3$.

From the above findings, a competition procedure can be performed using similar methodology. Assay plates such as the StreptaWell® microtiter plates used in the previously discussed optimization process are prepared by coating the wells with 10 pmol of biotinylated $PI(3,4,5)P_3$ per well. In a separate incubation apparatus, 10 pmol of LRP is preincubated with increasing amounts of closely related derivative PIPs. For example, the LRP is preincubated with either $diC_8$ $PI(3,4,5)P_3$ or $diC_8$ $PI(3,4,5)P_2$, prior to binding to the biotinylated $PI(3,4,5)P_3$ coated surface of the assay plate wells.

The results of the competition procedure can be determined by, for example, measuring absorbance (450 nm) for each of $PI(4,5)P_2$ and $PI(3,4,5)P_3$ at various pmol increments of competing PIP. Results of an example procedure are shown in FIG. 3. As shown in the graph of FIG. 3, $PI(4,5)P_2$ is able to compete weakly for binding, but $PI(3,4,5)P_3$ is a stronger competitor. The difference in competitiveness is particularly evident at lower levels of PIP, and the difference clearly exemplifies the ease of which the assay can distinguish between the two phosphoinositides.

Results from a second example further demonstrate the ability of the ELISA format for detection of PI 3-K activity. Recombinant PI 3-K αenzyme is incubated with 70 pmoles $diC_8$ $PI(4,5)P_2$ substrate for one hour. Enzyme activity is stopped and the reaction mixtures are pre-incubated with LRP, then tested in a competition binding assay, in the above example. FIG. 4 shows quantitation of substrate conversion to $PI(3,4,5)P_3$ and the effect of the addition of 50 μM LY29004, a compound which acts as a PI 3-K inhibitor.

A standard curve in which increasing amounts of $PI(3,4,5)P_3$ competitor is added to the assay is run alongside the enzyme reactions. The degree of $PI(4,5)P_2$ conversion to $PI(3,4,5)P_3$ is then estimated by comparing the values obtained for the reaction mixtures in the competition ELISA. After a one hour incubation with the enzyme, about 50 pmoles of $PI(3,4,5)P_3$ are generated, indicating that most of the $PI(4,5)P_2$ substrate has been converted. The presence of LY29004 blocks the enzyme activity to the extent that only a few picomoles of $PI(4,5)P_2$ is converted to $PI(3,4,5)P_3$. These results confirm the suitability of the ELISA format for determination of PI 3-K activity. These results also exhibit the suitability of this approach in an ELISA-based PI 3-K assay kit which is of use to individual researchers, and overcomes the shortcomings of the radioactive labeling and separation methods which are used in the related art.

Additional tests reveal that the assay of the present invention can be used to distinguish mixtures of lipids containing different ratios of $PI(4,5)P_2$ and $PI(3,4,5)P_3$. For example, a competition experiment involves the preincubation of 10 pmol of LRP with 10 pmol of total lipid containing different mixtures of $PI(4,5)P_2$ and $PI(3,4,5)P_3$ prior to binding these compounds to biotinylated $PI(3,4,5)P_3$ coated plates. The ability of the detector protein to distinguish between differences in the amount of $PI(3,4,5)P_3$ that is present can be determined by measuring absorbance (450 nm) for each of numerous samples. As shown in FIG. 4, some of the competition mixture samples included percentages of $PI(3,4,5)P_3$:$PI(4,5)P_2$ of 0:100, 10:90, 20:80, 30:70, 40:60, 50:50, 100:0, and samples that omitted competing PIP lipids, LRPs, biotinylated $PI(3,4,5)P_3$, and horseradish peroxidase (HRP), conjugated secondary antibody. The results in FIG. 4 show that the ability of the LRP detector protein to distinguish between differences in the amount of $PI(3,4,5)P_3$ that is present appears to be more sensitive when $PI(3,4,5)P_3$ is present at less than 50% of the lipid mixture.

Most experiments testing for lipid kinase activity exemplify actual cellular conditions in vivo where the level of substrate conversion is approximately 5 to 15%. Because the ability of the LRP detector protein to distinguish between differences in the amount of $PI(3,4,5)P_3$ that is present appears to be more sensitive when $PI(3,4,5)P_3$ is present at less than 50% of the lipid mixture, the assay of the present invention is well suited for detecting differences in the range for which tests are commonly performed. Further, the discovery of the LRP's ability to distinguish between various phosphoinisotides at various ratios exhibits the ability of the assay to be detect PI 3-K activity in vitro, as next discussed.

In Vitro ELISA Assay

To perform an assay for detection of PI 3-K activity in vitro, cell lysate containing active recombinant PI 3-K is mixed with 20 μg $diC_8$ $PI(4,5)P_2$ in a reaction buffer containing 2.5 mM $MgCl_2$, 5 mM HEPES, pH 7.0, and 25 μM ATP. The PI 3-K inhibitor wortmannin (200 nM) is added to some reactions for purposes of comparison with reactions not containing inhibitor. Reaction mixes are incubated at room temperature for 1 hour. Lipids are extracted from the reaction mixture, dried down, and re-suspended in water. The re-suspended samples are incubated with 10 pmol LRP and tested in the competitive ELISA. Results of this example are shown in FIG. 5. As shown, absorbance (450 nm) is remarkably lower after one hour of incubation for samples without PI 3-K inhibitor. Thus, an increase in competition for LRP binding is seen after the $PI(4,5)P_2$ incubation with the enzyme. Competition is decreased in samples containing wortmannin, presumably due to inhibition of kinase activity and less conversion of $PI(4,5)P_2$ to $PI(3,4,5)P_3$. These results establish the feasibility of using LRPs as detection reagents in vitro for determination of PI 3-K activity as modulated by kinase inhibitors.

The above embodiments of the present invention demonstrate a novel plate-based assay such as an ELISA assay for detection of $PI(3,4,5)P_3$ using a recombinant LRP, GST-Grp1-PH as a detection device. The novelty of the LRP specificity for $PI(3,4,5)P3$ in a competition ELISA is also demonstrated, as well as the detection of PI 3-K activity in vitro, and the inhibition of kinase activity by the inhibitor wortmannin using this approach. Of course, a variety of kinase inhibitors and potential inhibitors can be applied to the in vitro assay.

Amplified Luminescence Proximity Homogeneous Assay (ALPHA) Using LRP Detector Protein The principles of the present invention can also be applied to other assay methods, such as the type using AlphaScreen® reagents and the Fusion Alpha Universal Microplate Analyzer from Packard Bioscience®. The AlphaScreen® system detects emission shifts due to reactions involving oxygen singlets. More particularly, the system uses photosensitive donor beads which convert ambient oxygen to a singlet state upon illumination at 680 nm. If an acceptor bead is in close proximity to the donor bead, due to a biological interaction, the diffusion of singlet oxygen activates chemiluminscent receptors and fluorescent acceptor molecules on the bead, resulting in an emission shift from 520 to 620 nm.

According to the principles of the present invention, streptavidin-coated donor beads and acceptor beads coated with anti-GST are incubated with biotinylated $PI(3,4,5)P_3$ and the LRP detector protein before analysis. In order to establish the lipid to protein ratio that gives the best results, a standard curve $PI(3,4,5)P_3$ binding experiment is first performed.

As an example of the binding experiment, one pmol of LRP is incubated with increasing amounts of biotinylated $PI(3,4,5)P_3$ in a 25 μl reaction volume. Streptavidin-coated donor beads and anti-GST antibody acceptor beads (5 μl each, 20 μg/ml final concentration) are then added to the reaction mix. Following a 2 hour incubation, luminescence is measured. The measurement can be made using the AlphaScreen® mode on a Fusion Universal Microplate Analyzer (Packard Bioscience). Results are shown in FIG. 6, with luminescence measured according to increasing pmol amounts of biotinylated PI(3,4,5)P$_3$ added to the LRP. As shown in FIG. 6, an increase in luminescence with the addition of increasing amounts of biotinylated PI(3,4,5)P$_3$ to the reaction is observed.

A competition assay is then performed, the results of which are shown in FIG. 7. In the competition assay, the LRP is preincubated with increasing pmol amounts of PI(3, 4,5)P$_3$. As an example, LRP (1 pmol) is preincubated with increasing amounts of competing PI(3,4,5)P$_3$ for 1.5 hours. The LRP is then added to 1 pmol biotinylated PI(3,4,5)P$_3$, and 5 µl donor and acceptor beads. Luminescence is measured following an additional 2 hours of incubation. As shown in FIG. 8, luminescence decreases as the interaction of biotinylated PI(3,4,5)P$_3$ on the donor beads and LRP on the acceptor beads is competitively displaced by unlabeled PI(3,4,5)P$_3$.

As another example, using an ALPHA assay technique the luminescent assay for detection of changes in PI(3,4,5)P$_3$ levels in a background of PI(4,5)P$_2$ is tested to mimic the substrate conversion which occurs in an enzymatic assay. The results of this test reveal that increasing PI(3,4,5)P$_3$ in a background of PI(4,5)P$_2$ yields a competition profile which is virtually identical to that created by a standard curve of increasing PI(3,4,5)P$_3$ competitor alone, as shown in FIG. 9. Thus, comparison of values obtained from enzymatic reactions can be compared to a standard curve of increasing PI(3,4,5)P$_3$ to allow determination of the level of substrate conversion which has occurred. To allow for greater ease of performing this analysis, the data is converted to a logarithmic scale.

Figure 10:
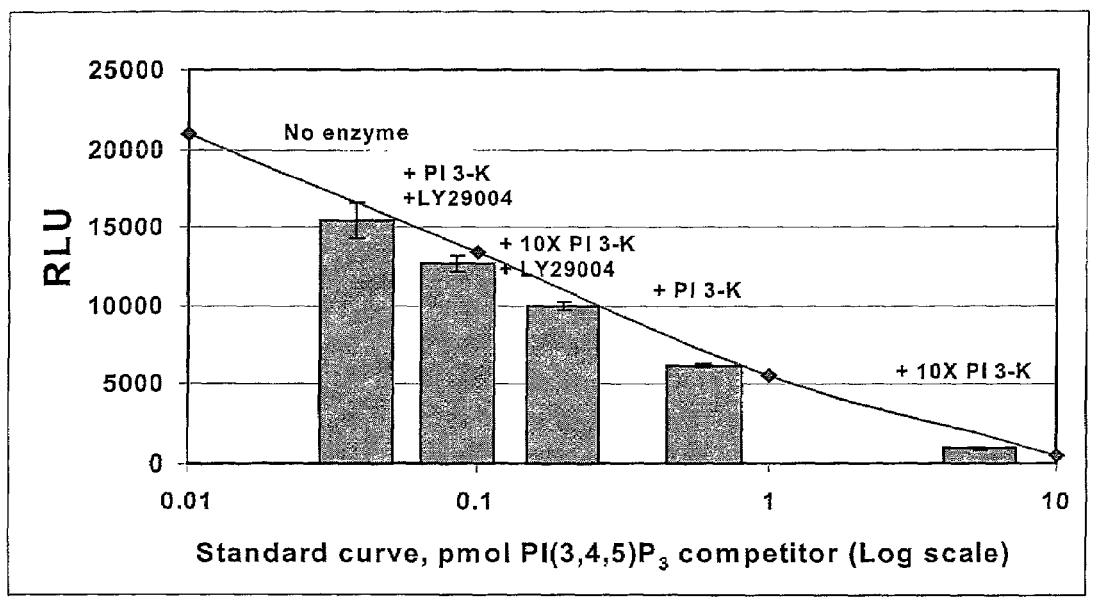
FIG. 10 shows a graphical representation of the results of an ALPHA test of kinase activity using purified, recombinant PI 3-Kα enzyme.

Another example tests the ability and sensitivity of the ALPHA assay for detection of PI 3-K activity. FIG. 10 shows the results of a test of kinase activity using purified, recombinant PI 3-Kα enzyme. 10 pmols of PI(4,5)P$_2$ substrate is incubated with varying amounts of PI 3-Kα in the presence and absence of 50 µM LY29004 for one hour. The resulting lipid mixtures are used to compete for the interaction of LRP coated donor beads with PI(3,4,5)P$_3$ coated acceptor beads in the ALPHA assay. Conversion of PI(4,5)P$_2$ to PI(3,4,5)P$_3$ is evident in the increased competition and decreased luminescent signal in samples containing PI 3-Kα. The addition of ten times more enzyme results in almost complete substrate conversion to PI(3,4,5)P$_3$. The activity of the enzyme is inhibited at least ten-fold by the presence of LY29004.

Figure 11:
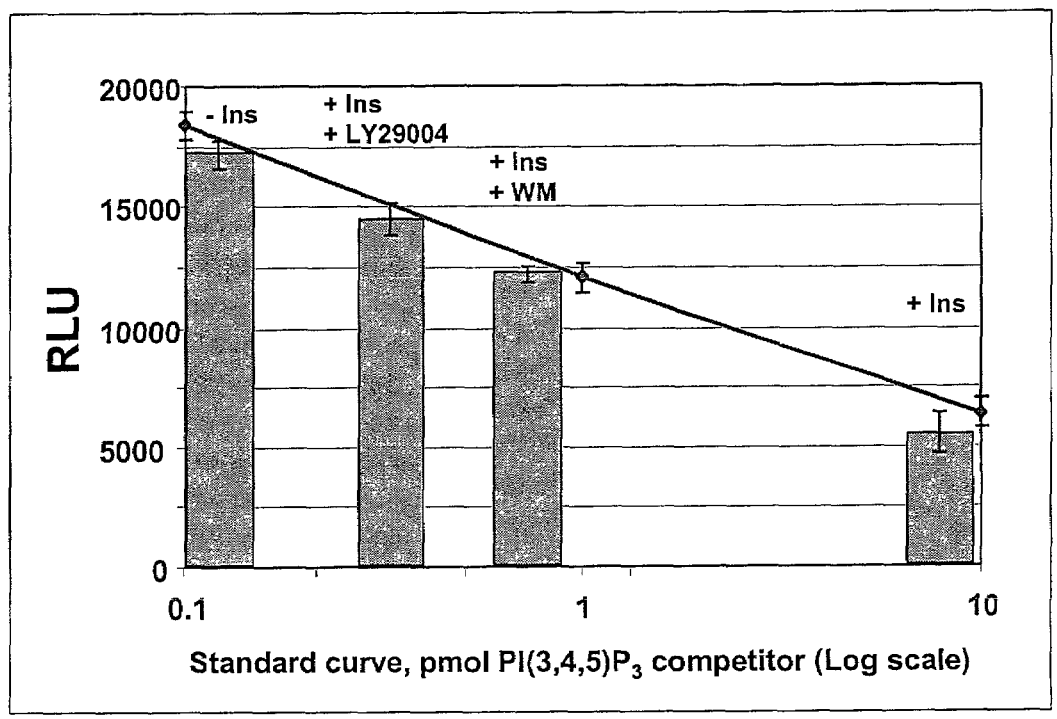
FIG. 11 shows a graphical representation of the results of an ALPHA test of kinase activity in vitro, in the presence of inhibitor.

The results from a similar experiment are shown in FIG. 11. In this case, NIH 3T3 cells are used as the source of PI 3-K. Cells are stimulated with AMOUNT insulin to activate PI 3-K. Cells are then lysed, and PI 3-K is recovered from the cell lysate by immunoprecipitation using a polyclonal antibody against the p85 subunit. Aliquots of immunoprecipitated enzyme are incubated with 10 pmoles PI(4,5)P$_2$ substrate for one hour, with 50 mM LY29004 or AMOUNT wortmannin added to some samples. The resulting lipid mixtures are used to compete for the interaction of LRP coated donor beads with PI(3,4,5)P$_3$ coated acceptor beads in the ALPHA assay. In the absence of insulin stimulation, there is no measurable enzyme activity, while enzyme isolated from insulin-stimulated cells is able to convert most of the substrate to PI(3,4,5)P$_3$. The addition of LY29004 or wortmannin inhibits enzyme activity, considerably reducing the amount of substrate conversion.

These results validate the ALPHA assay as a sensitive measure of PI 3-K activity using a LRP as a detection reagent. We have demonstrated that our assay is suitable for both in vitro tests of enzyme activity and for determining the relative activity of PI 3-K isolated directly from cells.

The ALPHA assay format is an example of yet another assay method that can be used in accordance with the principles of the present invention. The ALPHA format has the advantages of high specificity and sensitivity, and requires significantly less protein and lipid reagents than the ELISA assay format.

Thus, the ALPHA assay can be performed using LRP-coated acceptor beads and PI(3,4,5)P$_3$-coated donor beads, and in competition experiments in which free PI(3,4,5)P$_3$ is shown to compete for interaction of the donor and acceptor beads. Using the principles set forth regarding ELISA assays, the ALPHA assay can be used to perform competition assays involving different amounts of PI(3,4,5)P$_3$ and other PIP$_n$s to establish a degree of specificity of PI(3,4,5)P$_3$ as a competitor, and to perform in vitro assays and screening panels of PI 3-K inhibitors.

Fluorogenic Assay Using LRPs

Further, the principles of the present invention can be readily applied to other assay formats for detection of lipids or associated enzyme activity using the LRP as a detection device. For example, a fluorogenic assay method would be suited for using an LRP as a detection reagent. Like the luminescence assay described above using the ALPHA format, a fluorogenic assay has the advantage of being easy to perform, with no requirement for washing steps, and minimal mixing and detection steps, which makes these assay formats ideal for adaptation to high throughput (HTS) systems.

The components involved in a fluorogenic assay method include a florophoreconjugated PI(3,4,5)P$_3$, and a quencher-labeled LRP. Interaction between the LRP and the labeled PI(3,4,5)P$_3$ results in fluorescence quenching, while reduced binding in the presence of competitor results in the restoration of a fluorescent signal. As examples of a fluorescent label for PI(3,4,5)P$_3$, BODIPY™ or FITC™, both produced by Echelon Research Laboratories, Inc. First, working concentrations of the labeled PI(3,4,5)P$_3$ suitable for detection are determined by making serial dilutions in, for example, a microtiter plate. Fluorescence is then measured using a plate reader such as a Gemini Fluorescence™ plate reader made by Molecular Devices. Tests using a BODIPY-FL-PI(3,4,5)P$_3$ indicate that a range of 1 to 20 pmol is sufficient for good detection. The LRP can be conjugated to, for example, Dabcyl-SE [4-((4-(dimethylamino)-phenyl)azo)benzoic acid, succinimidyl ester], a non-fluorescent molecule that absorbs in the range at which FITC and BODIPY fluoresce, and is produced by Molecular Probes. Dabcyl-SE is an amine-reactive probe for conjugation to proteins. QSY-7, a higher efficiency quencher, may be used as well.

Once ideal parameters for lipid and protein labeling are established, and the amounts suitable for use in this assay are determined, performing the assay is simply performed as follows. The quencher-LRP is preincubated with a mixture of unlabeled competitor lipids for approximately 1 hour. Then this mixture is added to the fluorescent-PI(3,4,5)P$_3$ in the wells of, for example, a 96-well microtiter plate, although a variety of plate sizes may be incorporated into the method. After 1–2 h of incubation, fluorescence is measured using a plate reader. The ability of the Dabcyl-LRP to interact with BODIPY-FL-PI(3,4,5)P$_3$ reveals a decrease in fluorescent signal upon addition of increasing amounts of quencher-labeled protein. Furthermore, the addition of excess unlabeled PI(3,4,5)P$_3$ results in an increase in fluorescence, as LRP binding to the BODIPY-PI(3,4,5)P$_3$ is competitively displaced.

Results from this fluorogenic essay method reveal that the assay is simple and rapid to perform, and ideal for adaptation to high throughput screening applications. Consequently, this type of assay is particularly advantageous to the drug discovery industry, for example.

Automation of the Assays

In addition to the above-described advantages of the assay methods of the present invention, the non-radioactive assay of using an LRP as a lipid detection reagent for assaying enzyme activity readily lends itself to automation. Assay platforms used in the non-radioactive assay can be used, for example, with an automatic analyzer such as the Fusion Universal Microplate Analyzer by Packard Bioscience. Such a device is easily integrated with automated systems for plate stacking, liquid handling and cell-based assays. Other automation can be applied to the process in order to increase the assay process rate, including a plate washer and harvester and plate scintillation counter, such as Orca/Biomek® instrumentation.

Detection of PI 3-K Activity in Biological Samples

The determination of PI 3-K activity and PI(3,4,5)P$_3$ levels in biological samples can also be determined using the plate-based assays described above. Although the mixture of lipids extracted from cells or tissues is complex, the principles of the present invention are adaptable to tissue or cellular extractions. However, because endogenous lipids are poorly soluble in aqueous solution, lipid extraction should be followed by rehydration and formation of micelles when necessary. Techniques for such extraction, rehydration, and micelle formation are disclosed by I. M. Bird, *Analysis of Cellular Phosphoinositides and Phosphoinositols by Extraction and Simple Analytical Procedures*, 27 Methods Mol. Biol. 227 (1994).

The present inventors have determined for the first time that increases in PI(3,4,5)P$_3$ levels occur in cells following growth factor stimulation and that PI(3,4,5)P$_3$ levels are elevated in some types of cancers. As mentioned above, a variety of published reports link PI 3-K activity or loss of PTEN activity to cancers. It is expected by the inventors that PI(3,4,5)P$_3$ levels are likely to be elevated in at least cervical, prostate, ovarian, lung, and colon cancer. Using lipids or PI 3-K extracted from these and other types of biological samples, the plate-based assays using LRPs are able to detect changes in PI 3-K activity in cells and tissues. Immunodetection using anti-PI(3,4,5)P3 antibody can be performed concurrently to confirm increases in cytoplasmic PI(3,4,5)P$_3$. In addition, changes in PI(3,4,5)P$_3$ and PI(4,5)P$_2$ ratios can be biochemically verified using lipid extractions and fractionation through thin layer chromatography.

Further, the principles of the present invention may be applied in a clinical assay setting. A clinical assay can be performed for PI 3-K activity that is suitable for analysis of small, less invasive clinical samples, such as blood, pap smears, and needle biopsies. As an example of this type of clinical application of the plate-based assay using LRPs, known amounts of PI(3,4,5)P$_3$ are added to samples of blood or serum prior to lipid isolation and analysis. Construction of a calibration curve showing PI(3,4,5)P$_3$ competition in the assay is then performed, and a measure of assay sensitivity to changes in PI(3,4,5)P$_3$ in these types of samples is then determined. Based on these determinations, the assay can be applied to samples of cells or biological fluid for direct detection of lipid without performing a lipid extraction.

Assay Kits and Apparatuses

Another embodiment of the present invention involves a rapid plate-based assay kit for PI 3-K activity, including lipids, plates, and detection reagents. Such kits will satisfy particular needs from clinical or research laboratory scientists, for example. A rapid plate-based assay apparatus can be used for HTS drug discovery efforts in the pharmaceutical industry, for example.

PI 3-K Assay Kits

As discussed above, the assay formats discussed above are partly designed to allow detection of PI 3-K activity in vitro and for determining PI(3,4,5)P$_3$ levels in cellular samples. A scientist may be interested in determining whether PI 3-K is activated in a tumor cell line or in response to treatment of a cell with a particular stimulus. Kits for performing the assays of the present invention allow in vitro determination of PI 3-K activity on PI(4,5)P$_2$ substrate using an enzyme that has been isolated from experimental samples by immunoprecipitation. ELISA-based assay kits designed for these applications can contain immobilized PI(3,4,5)P$_3$ in large plates such as 96- and 384-well plates, GST-LRP or antibody detection reagents, and the appropriate primary and secondary antibodies. Synthetic PIP$_n$s are also supplied as controls and as substrates for in vitro kinase assays.

A fluorogenic assay kit for use by laboratory research can include Dabcyl-LRP conjugate, fluorescently labeled PI(3,4,5)P$_3$, and synthetic PIP$_n$s as controls and substrates. A benchtop PI(3,4,5)P$_3$/PI 3-K detection kit using these assay formats can also be provided for use in in vitro assays of PI 3-K activity. In a clinical setting, the assay is designed for accurate determination of PI(3,4,5)P$_3$ levels in tissue, blood, and serum samples. A kit designed for use in a clinical setting can use either an ELISA or fluorogenic format, and would be similar to that designed for use in a research lab.

Preparation of lipids from clinical samples may require extraction and desiccation, then rehydration. Alternatively, direct determination of lipids without extraction of the lipids can be performed. Lipids isolated from PI(3,4,5)P$_3$-enriched samples and samples lacking PI(3,4,5)P$_3$ can be included as controls, along with synthetic PI(3,4,5)P$_3$ and other PIP$_n$s.

b) Apparatuses Involving a PI 3-K Assay Adapted to an HTS Platform

PI 3-K is an important target for anti-cancer drug development, and there is a need in the pharmaceutical industry for new methods of screening for PI 3-K inhibitors. In-vitro assays of the present invention are advantageous for the discovery of potential drugs targeting PI 3-K. Present methods involve costly and cumbersome radioactive extractions, while the present assay formats provide a less expensive, simple, and non-radioactive alternative.

The present assays for use in drug discovery are convertible to a HTS format. The amplified luminescence homogeneous proximity assay (ALPHA) and the fluorogenic assay formats are particularly well-suited for HTS applications. Automation of assay platforms can be performed using an automated liquid handling system interfaced to a Fusion Universal Microplate Analyzer™ made by Packard Bioscience. The system includes a multi-well pipettor/washer integrated with a plate-handling robot for highly accurate and simultaneous delivery of microvolumes of liquids in large plates such as a 96- and 384-well format. Transfer to the analyzer, sample analysis, and data collection is also be automated and computer controlled.

It will be appreciated that the present invention is not limited to any of the exact constructions that have been described above and illustrated in the accompanying drawings, and that various modifications and changes can be made without departing from the scope and spirit thereof. It is intended that the scope of the invention only be limited by the appended claims.

The preceding description has been presented only to illustrate and describe the invention. It is not intended to be exhaustive or to limit the invention to any precise form disclosed. Many modifications and variations are possible in light of the above teaching.

The preferred embodiment was chosen and described in order to best explain the principles of the invention and its practical application. The preceding description is intended to enable others skilled in the art to best utilize the invention in various embodiments and with various modifications as are suited to the particular use contemplated. It is intended that the scope of the invention be defined by the following claims.

What is claimed is:

1. A method for the quantification of phosphoinositide kinase activity, which comprises: exposing a test solution containing an unknown amount of a target lipid, wherein said target lipid is a phosphorylation product of a reaction between a phosphoinositide kinase that is added to said test solution and a substrate phosphoinositide lipid that is added to said test solution, to an analyte solution containing a protein having a phosphoinositide lipid recognition motif that interacts with said target lipid and a predetermined amount of a competing target lipid which is labeled by a non-radioactive signal, and measuring said signal wherein a decrease in signal correlates with an increase of the phosphoinositide kinase activity.

2. The method according to claim 1, wherein said protein has specificity for phosphoinositide products of phosphatidylinositol 3-kinase (PI 3-Kinase) activity.

3. The method according to claim 2, wherein said protein contains an affinity tag fusion with said lipid recognition motif.

4. The method according to claim 2, wherein said protein is selected from an anti-phosphatidylinositol(3,4,5)phosphate antibody, an anti-phosphatidylinositol(3)phosphate antibody, a lipid recognition protein with specificity for phosphatidylinositol(3,4,5)phosphate, and a lipid recognition protein with specificity for phosphatidylinositol(3)phosphate.

5. The method according to claim 1, wherein said phosphoinositide kinase is phosphatidylinositol 3-kinase (PI 3-Kinase), and said target lipid is a phosphorylation product of phosphatidylinositol 3-kinase (PI 3-Kinase) and a phosphoinositide substrate lipid.

6. The method according to claim 5, wherein said phosphorylation product of the reaction of phosphatidylinositol 3-kinase (PI 3-Kinase) with a substrate lipid is phosphatidylinositol(3,4,5)phosphate or phosphatidylinositol(3) phosphate.

7. The method according to claim 1, wherein said method is accomplished using a plate-based assay.

8. The method according to claim 7, wherein said assay is an enzyme linked immunosorbent assay (ELISA).

9. The method according to claim 7, which further comprises: prior to exposing said protein having a lipid recognition motif to a target lipid and a competing lipid, coating an assay plate with said competing lipid.

10. The method according to claim 9, wherein the coating step includes coating a streptavidin-coated plate with said competing lipid.

* * * * *

UNITED STATES PATENT AND TRADEMARK OFFICE
CERTIFICATE OF CORRECTION

PATENT NO. : 7,067,269 B2 Page 1 of 1
APPLICATION NO. : 09/991933
DATED : June 27, 2006
INVENTOR(S) : Beth E. Drees et al.

It is certified that error appears in the above-identified patent and that said Letters Patent is hereby corrected as shown below:

On Title Page
In the Bibliographic Data, item (56), "Other Publications", add the following references:

Gray, A. et al., The pleckstrin homology domains of protein kinase B and GRP1 (general a\receptor for phosphoinositides-1) are sensitive and selective probes for the cellular detection of phosphatidylinositol 3,4-bisphosphate and/or 3,4,5-phosphatidylinositol in vivo, Biochemical Journal, 344(3), 929-936 (1999).

Kavan, J. et al., Specificity and Promiscuity in Phosphoinositide Binding by Pleckstrin Homology Domains, Journal of Biological Chemistry, 273(46), 30497-30508 (1998).

Piccione, E., et al., Phosphatidylinositol 3-Kinase p85 SH2 Domain Specificity Defined by Direct Phosphopeptide/SH2 Domain Binding, Biochemistry, Vol. 32, No. 13, 3197-3202 (1993).

Signed and Sealed this

Twenty-third Day of January, 2007

JON W. DUDAS
*Director of the United States Patent and Trademark Office*